(12) United States Patent
Burchell et al.

(10) Patent No.: US 8,800,562 B2
(45) Date of Patent: Aug. 12, 2014

(54) RESUSCITATORS

(75) Inventors: Robert James Burchell, Baldock (GB); Mark Charles Oliver, St. Albans (GB); Brian Alan Willatts, Milton Keynes (GB)

(73) Assignee: Smiths Group PLC, London (GB)

( * ) Notice: Subject to any disclaimer, the term of this patent is extended or adjusted under 35 U.S.C. 154(b) by 1586 days.

(21) Appl. No.: 11/631,555

(22) PCT Filed: Aug. 25, 2005

(86) PCT No.: PCT/GB2005/003304
§ 371 (c)(1),
(2), (4) Date: Jan. 4, 2007

(87) PCT Pub. No.: WO2006/024826
PCT Pub. Date: Mar. 9, 2006

(65) Prior Publication Data
US 2007/0256689 A1    Nov. 8, 2007

(30) Foreign Application Priority Data
Sep. 3, 2004  (GB) .................................. 0419597.0

(51) Int. Cl.
*A61M 16/20* (2006.01)
*A61M 16/06* (2006.01)
*A61M 16/08* (2006.01)

(52) U.S. Cl.
CPC ............. *A61M 16/201* (2013.01); *A61M 16/06* (2013.01); *A61M 16/0883* (2013.01)
USPC ............. 128/205.24; 128/205.25; 128/204.18

(58) Field of Classification Search
USPC ............. 128/200.24, 202.28, 203.11, 204.18, 128/204.21, 204.23, 204.26, 204.27, 128/205.13–205.17, 205.24

See application file for complete search history.

(56) References Cited

U.S. PATENT DOCUMENTS

| 2,453,475 | A |   | 11/1948 | Tobias |            |
|-----------|---|---|---------|--------|------------|
| 3,566,866 | A |   | 3/1971  | Adams  |            |
| 3,610,236 | A | * | 10/1971 | Smilg  | 128/204.24 |
| 3,717,147 | A |   | 2/1973  | Flynn  |            |
| 3,874,378 | A | * | 4/1975  | Isaacson et al. | 128/205.24 |
| 4,121,584 | A | * | 10/1978 | Turner et al. | 604/246 |
| 4,200,781 | A | * | 4/1980  | Dummer | 200/522 |
| 4,250,876 | A | * | 2/1981  | Kranz  | 128/202.22 |
| 4,281,651 | A | * | 8/1981  | Cox    | 128/204.23 |
| 4,919,132 | A | * | 4/1990  | Miser  | 128/205.17 |
| 4,960,115 | A | * | 10/1990 | Ranciato | 602/23 |
| 5,520,170 | A | * | 5/1996  | Laswick et al. | 128/204.18 |
| 5,537,999 | A | * | 7/1996  | Dearman et al. | 128/205.25 |
| 5,651,361 | A | * | 7/1997  | Dearman et al. | 128/205.25 |
| 6,067,984 | A | * | 5/2000  | Piper  | 128/205.24 |
| 6,871,835 | B2 | * | 3/2005 | Parsons | 251/83 |
| 7,513,254 | B2 | * | 4/2009 | Ben et al. | 128/205.13 |

* cited by examiner

*Primary Examiner* — Annette Dixon
(74) *Attorney, Agent, or Firm* — Louis Woo

(57) ABSTRACT

A resuscitator has two separate, spaced controls (23) and (30) both of which can be actuated manually to open a valve (100) and deliver a breathing cycle of a maximum timed duration to a patient. One control (23) has a button (24) on the top (13) of the unit (1), which is pushed in to actuate. A ring (25) surrounds the button (24) and has cam profiles (122) that engage with cam pins (120) on the button to push and hold it down when rotated. The other control (30) is on the underside surface (14), facing the patient and adjacent the gas outlet (5). This control includes a toggle lever (31), which can be displaced laterally in two different planes to open the valve (100).

9 Claims, 5 Drawing Sheets

RESUSCITATORS

FIELD OF INVENTION

This invention relates to resuscitators of the kind including a hand-held unit having an inlet adapted to be connected to a source of breathing gas, an outlet for providing a supply of breathing gas to a patient, and an arrangement for providing breathing gas to the outlet.

BACKGROUND OF INVENTION

Resuscitators are used to supply breathing gas to a patient who may not be breathing spontaneously. Portable resuscitators may take the form of a resilient bag that is squeezed manually to supply a volume of air to the patient, the bag refilling with air when it is released so that a new volume of air can be supplied. Alternatively, the resuscitator is a mechanical device including a timing valve and various other controls and is connected to an oxygen cylinder, which both provides the breathing gas, or a part of this, and which may also provide the power to drive the components of the resuscitator. Examples of such resuscitators are described in GB 2174760, GB 2174609, EP 343818, EP 342883, EP 343824, GB 2282542, EP 691137, GB 2284159 and GB 2270629. These resuscitators are arranged to supply gas in a cyclic manner to the patient at a rate compatible with normal breathing. Conveniently, the controls of a resuscitator are provided adjacent the face mask to which the resuscitator is connected, as described in GB 2284159 and GB 2270629, so that the resuscitator can be controlled and the mask can be supported by the same hand.

Resuscitators are often used by emergency services and may need to be used where the patient is in an inaccessible position, such as trapped in vehicle wreckage. A paramedic may need to hold and operate the resuscitator at arms length in an inconvenient position, which can be difficult with conventional resuscitators.

It is an object of the present invention to provide an alternative resuscitator.

BRIEF SUMMARY OF INVENTION

According to one aspect of the present invention there is provided a resuscitator of the above-specified kind, characterised in that the unit includes first and second manually-operable controls accessible on the outside of the unit by which the user can initiate a supply of gas to the outlet, the first and second controls being spaced from one another and arranged such that each can be operated independently of the other.

The first and second controls are preferably located on opposed surfaces of the unit. The first control is preferably located adjacent the outlet. The first and second controls may be of different forms. The first and second controls are preferably arranged to initiate a single cycle with a limited maximum duration. The first control may include a toggle mounted at one end and operable by displacing the other end laterally. The second control may have a manually-displaceable member associated with it that is displaceable to a position where the second control is retained in an actuated position such that the unit delivers repeated timed cycles. The second control preferably includes a button that can be pushed inwardly of the unit to initiate supply of gas. The button and manually-displaceable member preferably have engaging cam features.

According to another aspect of the present invention there is provided a resuscitator including a hand-held unit having an inlet adapted to be connected to a source of breathing gas, an outlet for providing a supply of breathing gas to a patient, and an arrangement for providing breathing gas to the outlet, and a manually-operable control accessible on the outside of the unit by which the user can initiate a supply of gas to the outlet, characterised in that the control includes a toggle mounted at one end and operable by displacing the other end laterally.

The one end of the toggle is preferably arranged to displace a first member in a first direction when the other end of the toggle is displaced, the first member being coupled to a second member such that the second member is displaced by the first member in an opposite direction from the first member. The toggle is preferably located on a side of the unit that is, in use, adjacent the patient. The toggle may be located remote from the gas inlet and adjacent the gas outlet.

According to a further aspect of the present invention there is provided a valve mechanism for a resuscitator, characterised in that the mechanism includes a valve member displaceable along its length within a bore of a housing, a first manually-actuable member displaceable axially of the valve member to effect displacement of the valve member, and a second elongate manually-actuable member displaceable at one end laterally of its length and coupled at its opposite end with the valve member to effect displacement of the valve member.

A resuscitator according to the present invention will now be described, by way of example, with reference to the accompanying drawings, in which:

DETAILED DESCRIPTION OF INVENTION

Figure 1:
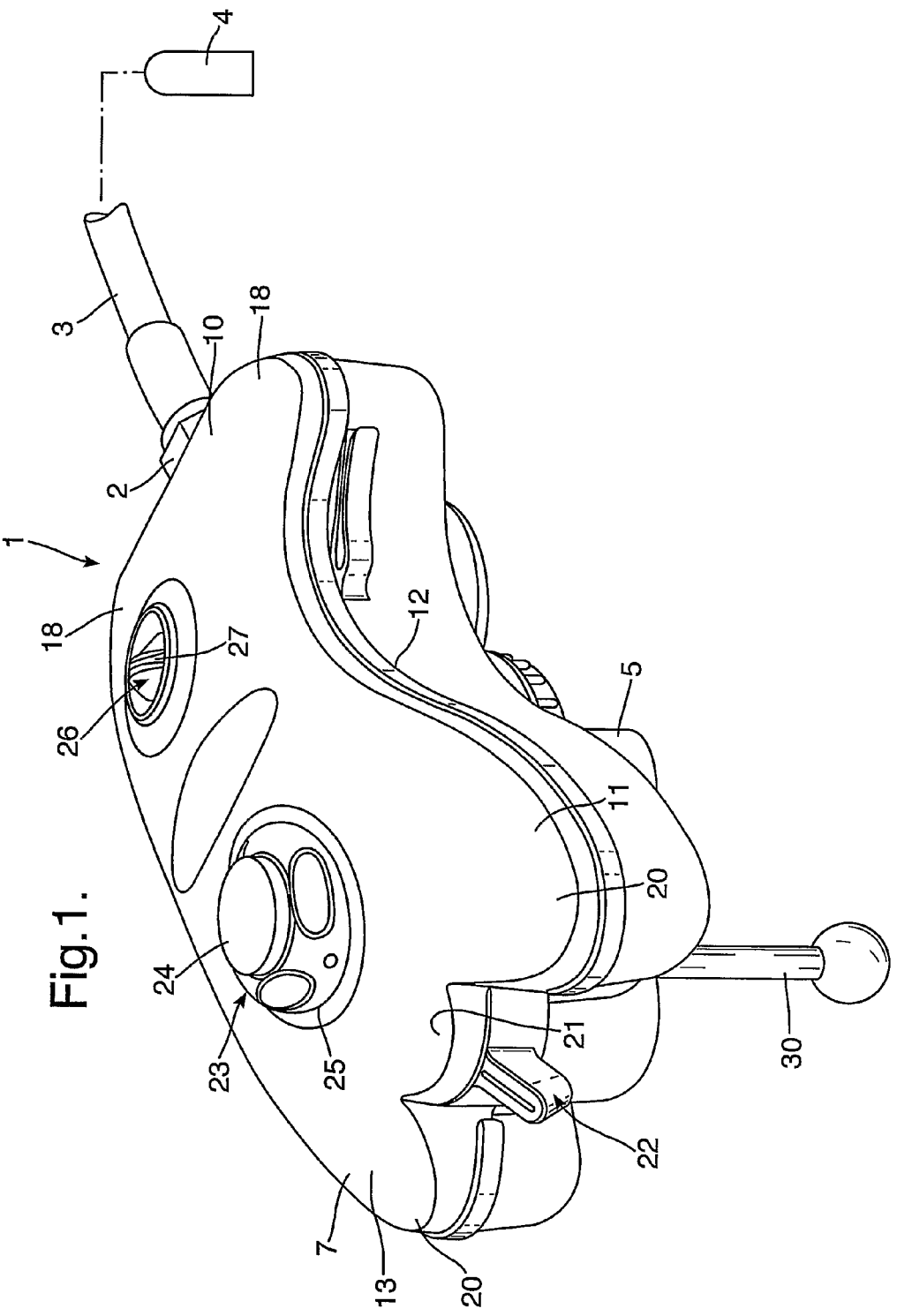
FIG. 1 is a perspective view of the upper surface of the resuscitator.
Figure 2:
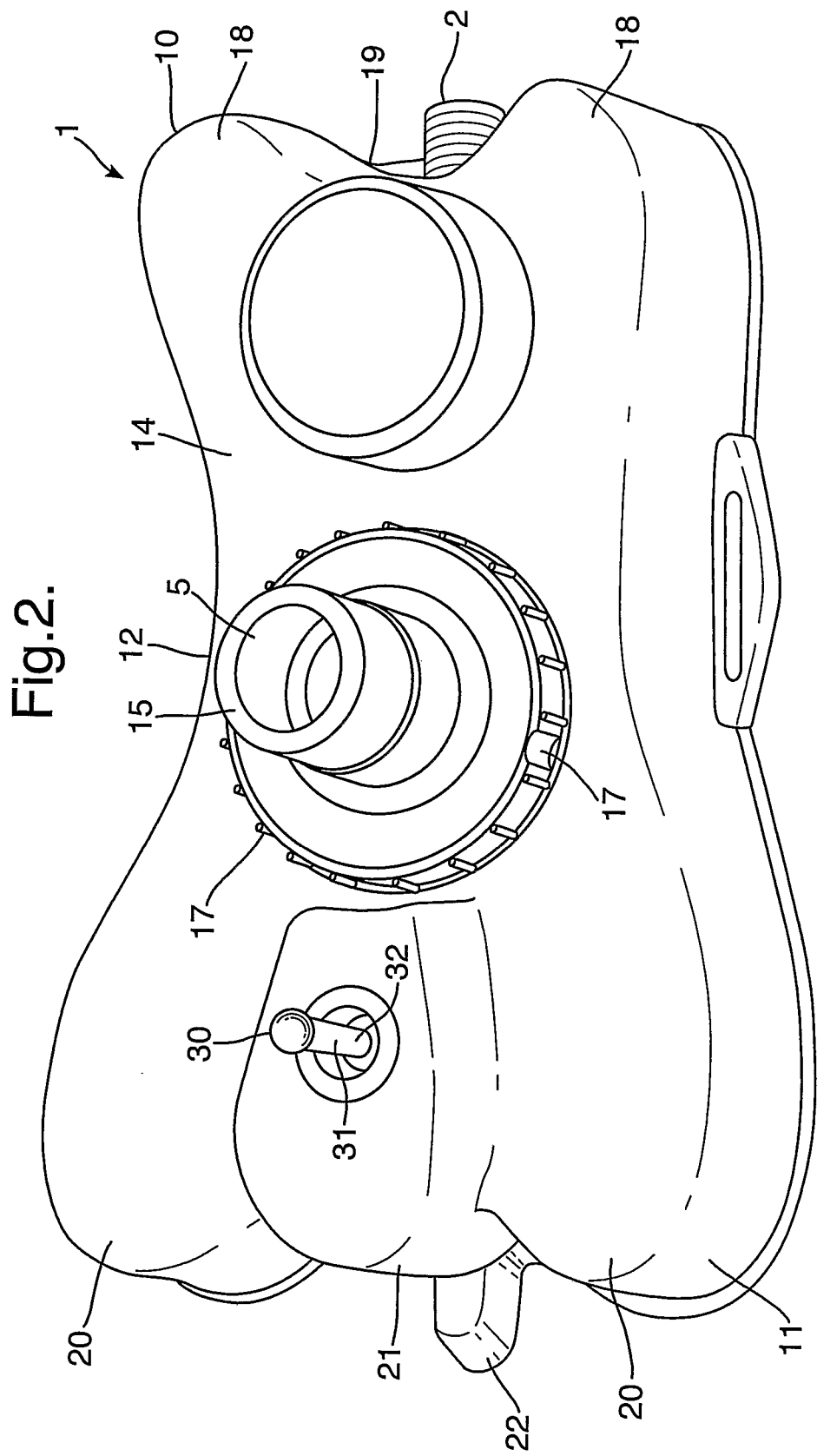
FIG. 2 is a perspective view of the underside of the resuscitator.
Figure 3:
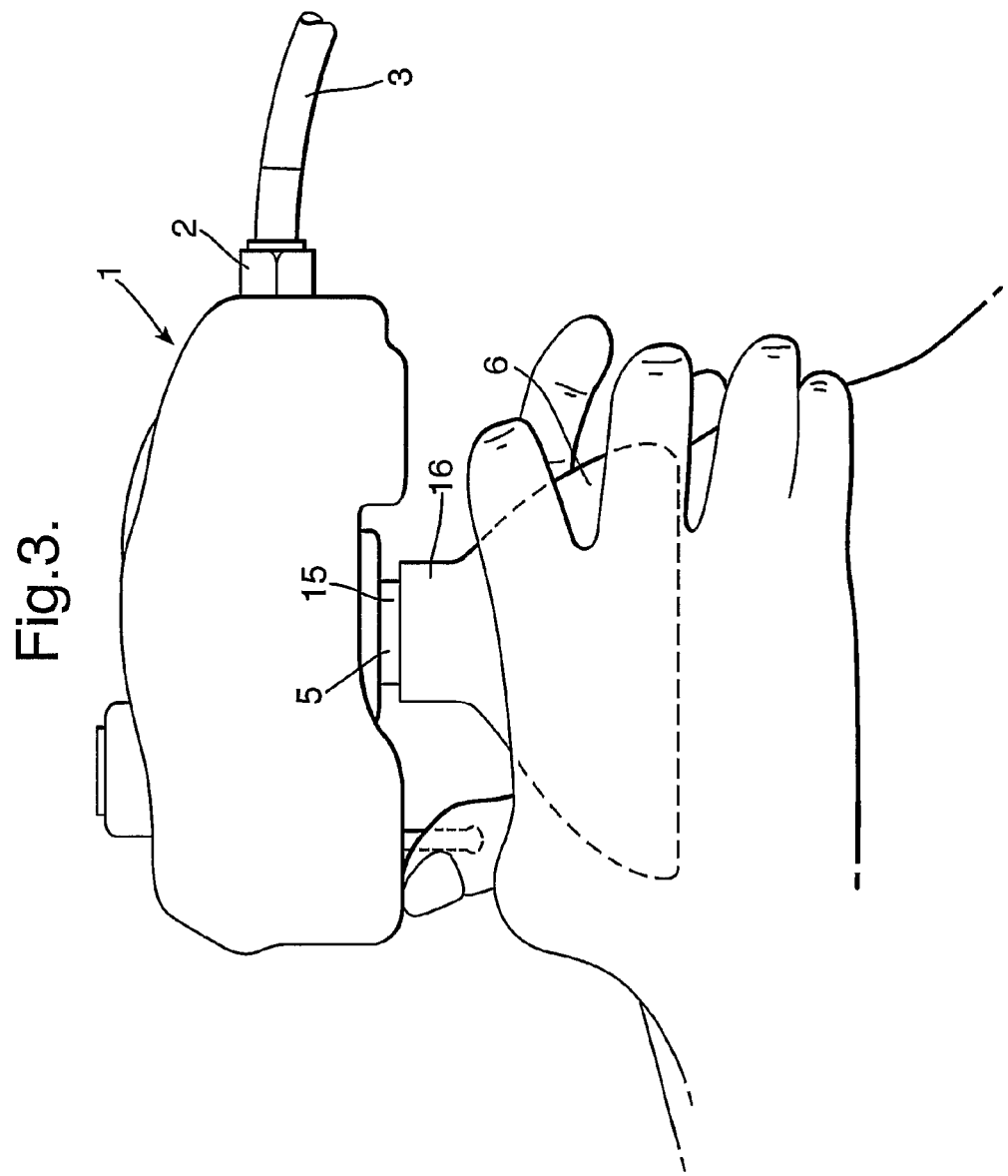
FIG. 3 is a side view of the resuscitator in use.

With reference first to FIGS. 1 to 3, the resuscitator comprises a hand-held unit 1 with an inlet 2 connected via a hose 3 to a source of breathing gas in the form of a pressurized cylinder 4 of oxygen. The unit 1 has an outlet 5 connected usually to a face mask 6, endotracheal tube or the like. The unit 1 includes gas circuits, valves and the like by which flow of gas from the inlet 2 to the outlet 5 is controlled. Various manually-operable controls, as will be explained later, are disposed on the casing 7 of the unit 1 so that the user can alter the functioning of the unit.

Figure 4:
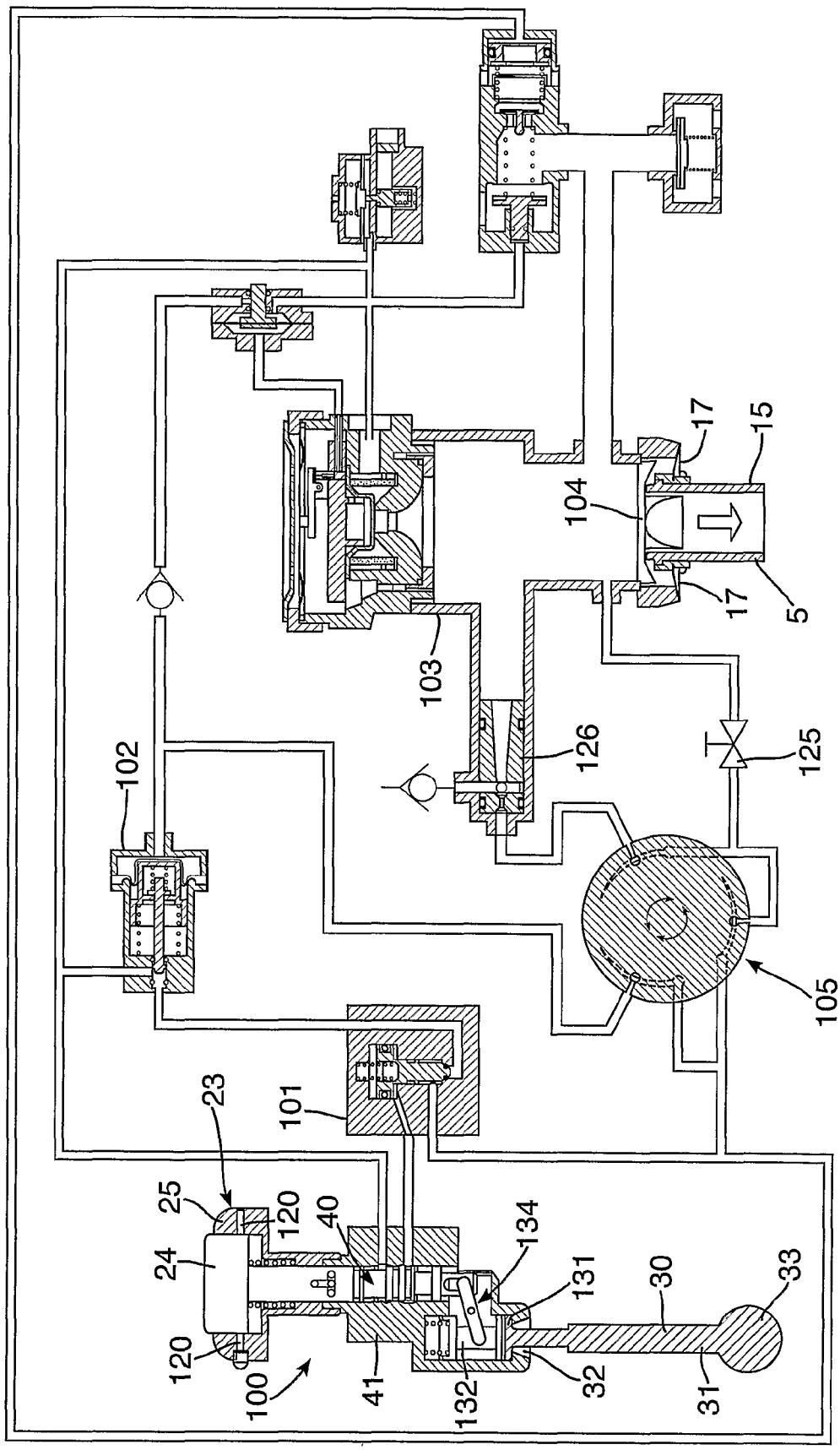
FIG. 4 is a circuit diagram of the resuscitator.

The circuit within the casing 7 is shown in FIG. 4 although an understanding of the detail of the circuit is not needed to understand the present invention. The circuits and components within the unit 1 operate in two different modes. In the usual "automatic" mode the unit 1 provides a cyclical supply of breathing gas that automatically repeats at a regulated frequency and with a regulated tidal volume. In the alternative "manual" mode the unit 1 delivers cycles of gas only when initiated by the user; this is used when the user needs greater control of patient ventilation. The length of this single cycle of gas is determined by the user but cannot exceed a maximum duration. If the user delivers only a shortened inspiratory phase he can deliver another inspiratory phase immediately afterwards but the duration of this second inspiratory phase is proportional to the incomplete volume not previously delivered and to the time that has elapsed since the last delivery of gas, that is the time of the expiratory phase that has elapsed. This arrangement ensures that it is not possible to deliver two or more full breaths in very close succession and thereby avoids the risk of over inflating the patient. If a full tidal volume is delivered, the circuit will prevent any further delivery until the full expiratory time has passed.

Briefly, the circuit includes a manual or momentary valve 100, which will be described in detail later. Operation of this valve 100 controls a bi-stable valve 101, which in turn controls the flow of oxygen between an oscillator/timer 102 and the input of a valve assembly 103, which provides the gas output to the outlet 5. The circuit is described in greater detail in WO2005/023349.

The casing 7 of the unit 1 is of moulded plastics with a figure of eight shape when viewed from above in plan, having two enlarged, rear end portions 10 and 11 and a waisted, narrower central portion 12. This shape allows the user to grip the unit securely about the central portion 12. The upper surface 13 of the casing 7 is slightly domed between its ends and across its width. The opposed lower surface 14 has the same shape but is substantially flat. The outlet 5 is located in the centre of the lower surface 14. This has a conventional male taper coupling 15 adapted to mate with a female coupling 16 on the face mask 6 or tracheal tube. The valve assembly 103 includes a conventional patient valve 104, which allows gas to flow from the unit 1 to the coupling 15 but diverts exhaled gas from the patient to atmosphere via openings 17 around the outlet.

The rear end portion 10 of the casing 7 has two side ears 18 and a central curved recess 19 in which the gas inlet 2 is located and protected by the side ears. The forward end portion 11 has a similar shape with two side ears 20 but has a central, curved protrusion 21 supporting a control lever 22. The lever 22 is pivoted at one end within the casing 7 and is coupled to a flow control device 105 within the unit in the form of a grooved disc, which is rotated by displacement of the lever 22 to adjust the tidal volume of gas supplied to the patient. The other end of the lever 22 projects from the protrusion 21 so that the user can position it laterally against markings on the casing 7 to select the desired tidal volume to be administered. Adjusting the tidal volume also automatically alters the frequency of the ventilation cycles in a manner described in WO2005/023349. The ears 20 help protect the lever 22 from being inadvertently displaced.

Figure 6:
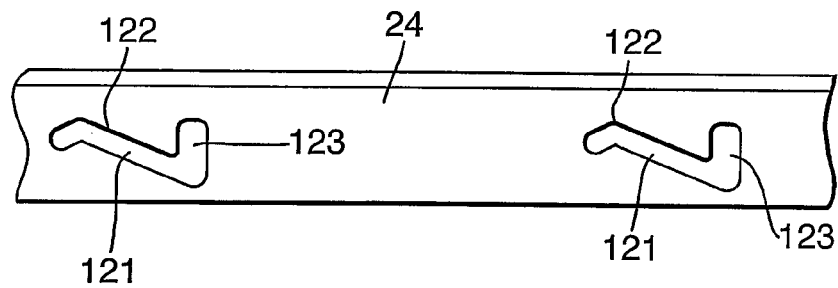
FIG. 6 illustrates cam profiles within the control valve.

The upper surface 13 of the casing 7 supports two further user-operable controls. One control 23 is located towards the forward end of the casing and takes the form of a circular button 24 surrounded by an encircling ring 25. The ring 25 is rotatable through about 45° between two positions. In one position, "Manual", the button 24 can be pushed inwardly of the casing 7 by the user to displace a spool 40 down a bore within the housing 41 of the momentary valve 100. This opens the momentary valve 100 and allows gas to flow to the bistable valve 101 and initiates the start of a single ventilation cycle. When the button 24 is pushed in, an oxygen or oxygen/air mixture is delivered to the patient for as long as the button is held in but up to a maximum time of one full cycle. If the button 24 is pushed and held in, the unit 1 continues delivering inspiratory and expiratory ventilation cycles one after the other until the button is released. By releasing the button 24 early the user can choose to give a shorter duration delivery of gas. When the ring 25 is rotated to its other position, "Automatic", two cam pins 120 projecting radially inwardly of the ring engage an inclined portion 121 of two cam profiles 122 (as shown in FIG. 6) formed diametrically opposite one another on the outside of the button 24, thereby pushing and holding down the button. In this way, the button 24 is held in the actuated position and the resuscitator delivers repeated timed ventilation cycles one after the other. When the ring 25 is in its "Manual" setting, the cam pins 120 align with vertical sections 123 of the cam profiles 122 so that movement of the button 24 is not impeded.

The other control on the upper surface 13 is an optional air-mix control 26. This takes the form of a circular knob 27, which can be twisted between one of two different positions. One position may be marked "100%", to indicate that the ventilator is set to deliver pure oxygen; the other may be marked "50%", to indicate that the ventilator is set to deliver 50% oxygen and 50% air. The knob 27 is connected within the casing 7 to a switch 125 that diverts oxygen to an air entrainment device 126 so that the oxygen entrains atmospheric air when the control is in the 50% position. The knob mechanism 27 has a detent for the 50% position and is sprung loaded so that it returns to the 100% position if not fully engaged in the 50% position. This reduces the risk of the knob 27 being inadvertently displaced out of the 100% setting. In some resuscitators this air-mix control 26 may be omitted and the resuscitator would only be capable of delivering pure oxygen.

Figure 5:
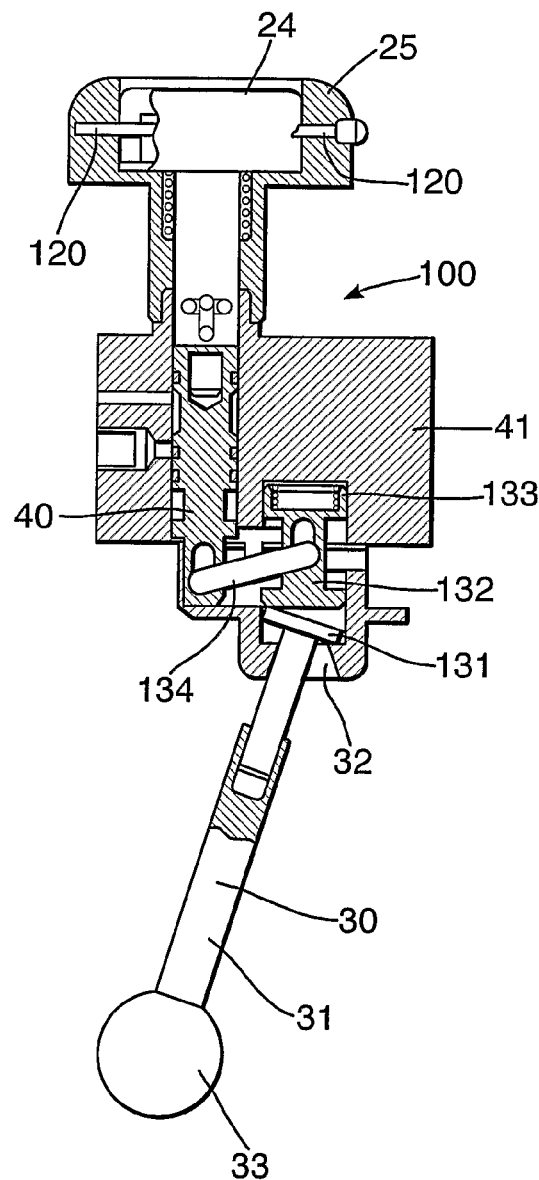
FIG. 5 is a cross-sectional view of the momentary control valve when opened by actuation of the toggle on the underside of the resuscitator.

With reference now also to FIG. 5, the resuscitator has a further user-actuable control 30 on the lower surface 14, that is, the surface that, in use, is adjacent the patient. The control 30 is located towards the forward end of the lower surface, adjacent the outlet 5, remote from the inlet 2, and between the outlet and the tidal volume control lever 22. The control 30 duplicates the button 24 on the upper surface 13 in that both control operation of the manual, momentary valve 100 and either can be actuated to deliver ventilation cycles to the patient. The control 30 takes the form of a short rod-like lever, toggle or joy-stick 31 projecting vertically down from the lower surface 14 from within a surrounding circular aperture 32. The upper, inner end of the toggle 31 has a flat, enlarged head 131, which engages the lower surface of a follower or bobbin 132. The bobbin 132 is slidable vertically and is urged downwardly into contact with the head 131 by a helical spring 133. The size of the aperture 32 relative to the toggle 31 is such as to enable the lower, free end 33 of the toggle to be displaced in any direction, that is, in any plane including the axis of the toggle, including orthogonal planes. When the toggle 31 is displaced at an angle it can be seen that this tilts the head 131 and hence pushes up the bobbin 132 against the action of the spring 133. When the toggle 31 is released, the spring 133 and bobbin 132 push the head 131 flat and hence urge the toggle 31 it to a natural, central position where it projects vertically downwards orthogonally to the lower surface 14. The bobbin 132 engages one end of a crank arm 134 pivoted midway along its length. The opposite end of the crank arm 134 is coupled to the lower end of the spool 40 such that when the free end 33 of the toggle 31 is moved laterally momentarily in any direction it rotates the crank arm and pulls down the spool 40 and the button 24, as shown in FIG. 5. This, therefore, initiates a single timed cycle in the same way as when the spool 40 is displaced by pushing directly on the button 24. If the toggle 31 is held displaced, it causes the unit 1 to deliver repeated cycles of breathing gas, one after the other, until the toggle is released. The toggle 31 can be released before a fall cycle is completed in order to shorten the duration of an inspiratory phase. The joystick action of the control 30 enables the user to operate the resuscitator from various different positions even if the resuscitator is held at arms length from one side, it also facilitates operation in situations where the region around the patient's face is obstructed. The toggle control 30 may have advantages even in resuscitators where this is the only manual control.

Duplicating the manual operation control on two opposed surfaces of the resuscitator facilitates operation of the resuscitator in a variety of different situations. It will be appreciated that alternative resuscitators could have two manually-operable controls spaced from one another at different locations instead of on the upper and lower surfaces. The controls could take various different forms. For example, both controls could be push buttons or both could be toggles, or they could be any combination of different forms of controls.

The invention claimed is:

1. A resuscitator including a hand-held unit having an inlet adapted to be connected to a source of breathing gas, an outlet for providing a supply of breathing gas to a patient, and an arrangement including a timer for providing cycles of breathing gas of defined duration to the outlet, characterized in that the unit includes first and second manually-operable controls accessible on the outside of the unit, and that the first and second controls are both separately operable such that either can initiate the start of a breathing cycle of supply of gas to the outlet independent of operation of the other control, the first and second controls being spaced from one another and arranged such that each can be operated independently of the other.

2. A resuscitator according to claim 1, characterized in that the first and second controls are located on opposed surfaces of the unit.

3. A resuscitator according to claim 1, characterized in that the first control is located adjacent the outlet.

4. A resuscitator according to claim 1, characterized in that the first and second controls are of different forms.

5. A resuscitator according to claim 1, characterized in that the first and second controls are arranged to initiate a single cycle with a limited maximum duration.

6. A resuscitator according to claim 1, characterized in that the first control includes a toggle mounted at one end and operable by displacing the other end laterally.

7. A resuscitator according to claim 1, characterized in that the second control has a manually-displaceable member associated with it that is displaceable to a position where the second control is retained in an actuated position such that the unit delivers repeated timed cycles.

8. A resuscitator according to claim 1, characterized in that the second control includes a button that can be pushed inwardly of the unit to initiate supply of gas.

9. A resuscitator according to claim 8, characterized in that the button and manually-displaceable member have engaging cam features.

\* \* \* \* \*